United States Patent
Han

(10) Patent No.: US 11,124,424 B2
(45) Date of Patent: Sep. 21, 2021

(54) PROCESS FOR THE CO-PRODUCTION OF METHANOL AND AMMONIA IN PARALLEL

(71) Applicant: Haldor Topsøe A/S, Kgs. Lyngby (DK)

(72) Inventor: Pat A. Han, Smørum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/623,139

(22) PCT Filed: Jul. 20, 2018

(86) PCT No.: PCT/EP2018/069790
§ 371 (c)(1),
(2) Date: Dec. 16, 2019

(87) PCT Pub. No.: WO2019/020520
PCT Pub. Date: Jan. 31, 2019

(65) Prior Publication Data
US 2020/0207632 A1    Jul. 2, 2020

(30) Foreign Application Priority Data

| Jul. 25, 2017 | (DK) | PA 2017 00425 |
| Sep. 25, 2017 | (DK) | PA 2017 00522 |
| May 28, 2018 | (DK) | PA 2018 00237 |
| Jul. 6, 2018 | (DK) | PA 2018 00345 |
| Jul. 6, 2018 | (DK) | PA 2018 00351 |
| Jul. 6, 2018 | (DK) | PA 2018 00352 |

(51) Int. Cl.
| *C01C 1/04* | (2006.01) |
| *C01B 3/02* | (2006.01) |
| *C01B 3/38* | (2006.01) |
| *C01C 1/02* | (2006.01) |
| *C07C 29/151* | (2006.01) |
| *C25B 1/04* | (2021.01) |

(52) U.S. Cl.
CPC ............ *C01C 1/0488* (2013.01); *C01B 3/025* (2013.01); *C01B 3/382* (2013.01); *C01C 1/024* (2013.01); *C07C 29/1518* (2013.01); *C25B 1/04* (2013.01); *C01B 2203/0216* (2013.01); *C01B 2203/0283* (2013.01); *C01B 2203/046* (2013.01); *C01B 2203/061* (2013.01); *C01B 2203/068* (2013.01)

(58) Field of Classification Search
CPC ... C07C 29/1518; C01C 1/0488; C01C 1/024; C25B 1/04; C01B 3/025; C01B 3/382; C01B 2203/0216; C01B 2203/061
See application file for complete search history.

(56) References Cited

U.S. PATENT DOCUMENTS

| 4,479,925 A | 10/1984 | Shires et al. |
| 4,792,441 A | 12/1988 | Wang et al. |
| 2004/0182002 A1 | 9/2004 | Malhotra et al. |
| 2007/0256360 A1 | 11/2007 | Kindig et al. |
| 2007/0299144 A1 | 12/2007 | Davey et al. |
| 2009/0165459 A1 | 7/2009 | Henriksen et al. |
| 2010/0076097 A1 | 3/2010 | Metz et al. |
| 2012/0091730 A1 | 4/2012 | Stuermer et al. |
| 2012/0100062 A1 | 4/2012 | Nakamura et al. |
| 2013/0072583 A1 | 3/2013 | Koskinen et al. |
| 2013/0345325 A1 | 12/2013 | Lecomte et al. |
| 2014/0357736 A1* | 12/2014 | Dahl .................. C07C 29/1518 518/702 |
| 2016/0115405 A1 | 4/2016 | Zubrin et al. |

FOREIGN PATENT DOCUMENTS

| EP | 2 166 064 A1 | 3/2010 |
| EP | 2 192 082 A1 | 6/2010 |
| EP | 2 589 574 A1 | 5/2013 |
| EP | 2 676 924 A1 | 12/2013 |
| EP | 2 805 914 B1 | 9/2017 |
| GB | 2545474 A | 6/2017 |
| KR | 10-2005-0075628 A | 7/2005 |
| WO | WO 2007/049069 A1 | 5/2007 |
| WO | WO 2010/008494 A1 | 1/2010 |
| WO | WO 2011/088981 A1 | 7/2011 |
| WO | WO 2012/084135 A1 | 6/2012 |
| WO | WO 2015/067436 A1 | 5/2015 |
| WO | WO 2015/128456 A1 | 9/2015 |
| WO | WO 2016/008820 A1 | 1/2016 |

OTHER PUBLICATIONS

K. H. Kaggerud et al., "Chemical and Process Integration: Synergies in Co-Production of Power and Chemicals from Natural Gas with $CO_2$ Capture", Applied Thermal Engineering, Pergamon, Oxford, GB, vol. 26, No. 13, Sep. 1, 2006, pp. 1345-1352.

* cited by examiner

Primary Examiner — Jafar F Parsa
(74) Attorney, Agent, or Firm — Blank Rome LLP

(57) ABSTRACT

A process for co-production of methanol and ammonia in parallel based on autothermal reforming with oxygen enriched air from electrolysis of water and separation of air and preparation of ammonia with hydrogen from the electrolysis of water and nitrogen from the separation of air.

4 Claims, No Drawings

PROCESS FOR THE CO-PRODUCTION OF METHANOL AND AMMONIA IN PARALLEL

The present invention is directed to the parallel co-production of methanol and ammonia. More particular, the invention is based on electrolysis of water for the preparation of hydrogen and oxygen, and separation of air for the preparation of nitrogen and oxygen. The oxygen from the electrolysis and air separation is employed for the preparation of methanol synthesis gas by autothermal steam reforming of a hydrocarbon feed stock and the nitrogen from the air separation and the hydrogen from the electrolysis is in a parallel process stage employed in synthesis of ammonia.

In the conventional methanol process, synthesis gas is typically prepared in so-called two step reforming process. In the two-step reforming process, a desulfurized hydrocarbon feed stock, usually natural gas, is primary reformed in a fired primary steam methane reformer (SMR) and subsequently in an adiabatic secondary steam reformer by partial oxidation of hydrogen and hydrocarbons and adiabatic steam reforming of residual amounts of hydrocarbons from the partial oxidation step. The adiabatic secondary reformer is operated with essentially pure oxygen for use in the partial oxidation step. The essentially pure oxygen is typically supplied from an Air Separation Unit (ASU).

Alternatively, to the 2-step reforming, stand-alone SMR or stand-alone autothermal reforming can be used to prepare the synthesis gas.

Regardless of whether stand-alone SMR, 2-step reforming, or stand-alone ATR is used, the product gas will comprise hydrogen, carbon monoxide, and carbon dioxide as well as other components normally including methane and steam.

Ammonia synthesis gas is conventionally prepared by subjecting hydrocarbon feed of natural gas or higher hydrocarbons to endothermic steam reforming reactions in a fired tubular steam reformer by contact with a steam reforming catalyst. The primary reformed gas is then fed into an adiabatic secondary reformer, wherein part of hydrogen and residual amounts of hydrocarbons in the primary reformed gas are partial oxidized with oxygen enriched process air in presence of a secondary reforming catalyst. From the secondary reformer, raw synthesis gas containing hydrogen, nitrogen, carbon monoxide and carbon dioxide formed during reaction of the feedstock in the above steam reforming reactions and nitrogen introduced into the gas through addition of air in the secondary reforming step.

Recently, a combination of electrolysis of water for production of hydrogen and air separation to produce nitrogen has been envisaged for the preparation of ammonia synthesis gas. The thus produced hydrogen and nitrogen are combined in stoichiometric ratios to form synthesis gas for ammonia production. The problem with the combination of electrolysis and air separation is, however, that oxygen is produced as by-product in both electrolysis and air separation, which has no use in the ammonia synthesis, and can be considered as energy losses.

Current processes for co-production of methanol and ammonia involve generally parallel processes in which a common reforming section is used to generate a synthesis gas which is split in separate parallel streams, one of which is used for methanol synthesis and the other for ammonia synthesis. The co-production of methanol and ammonia can also be conducted sequentially or in series, where the synthesis gas produced in the reforming section is first converted to methanol and the unreacted gas containing carbon oxides and hydrogen is subsequently used for ammonia synthesis. Water gas shift and/or carbon dioxide removal steps of the synthesis gas stream are required depending of the desired ratio of methanol product to ammonia product, thus involving the release of $CO_2$ to the atmosphere and the investment in highly expensive and complicated units for conducting the shift conversion and carbon dioxide removal.

The present invention is based on a combination of autothermal steam reforming using oxygen from the electrolysis of water and from an air separation (ASU) in the partial oxidation of hydrocarbon feed stock in the autothermal reforming process. Hydrogen from the electrolysis and nitrogen from the ASU in a parallel process used for the preparation ammonia synthesis gas.

Thus, this invention is a process for the co-production of methanol and ammonia in parallel comprising the steps of
  (a) providing a hydrocarbon feed stock;
  (b) preparing a separate hydrogen stream and a separate oxygen stream by electrolysis of water;
  (c) preparing a separate oxygen stream and a separate nitrogen stream by separation of air;
  (d) introducing at least part of the separate oxygen stream from step (b) and at least part of the separate oxygen from step (c) into an autothermal reformer;
  (e) in the autothermal reformer autothermal reforming the hydrocarbon feed stock from step (a) to a methanol synthesis gas comprising hydrogen, carbon oxides;
  (f) converting the methanol synthesis gas to raw methanol in a methanol synthesis stage; and in parallel
  (g) introducing the at least part of the separate hydrogen stream from step (b) and the separate nitrogen stream from step (c) into an ammonia synthesis loop and converting the nitrogen and hydrogen stream to ammonia.

Methanol synthesis gas preferably has a composition corresponding to a so-called module ($M=(H2-CO2)/(CO+CO2)$) of 1.9-2.2 or more preferably slightly above 2 (eg. 2.0-2.1). Depending on the composition of the hydrocarbon feed stock, the module in the methanol synthesis gas from the autothermal reforming step can be lower than preferred value. In such circumstances a part of the hydrogen from the water electrolysis can be added to the synthesis gas in order to adjust the module to the preferred value.

Thus, in an embodiment of the invention, module ($M=(H2-CO2)/(CO+CO2)$) of the methanol synthesis gas from step (e) is adjusted to a value of between 1.9 and 2.2 by adding a part of the separate hydrogen stream from step (b) into the methanol synthesis gas from step (e).

In further an embodiment all or a part of the hydrogen from the electrolysis is introduced together with nitrogen from the air separation unit into the suction section of a makeup gas compressor in the ammonia loop amounts to provide a molar ratio of the hydrogen to the nitrogen of 2.7-3.3 in the ammonia synthesis gas as prepared in step (g).

The advantages of the process according to the invention are essentially no or only a minor loss of energy in the water electrolysis and the air separation together with a reduced size of the ASU due to a part of the oxygen used in the autothermal reforming is produced by the water electrolysis.

In a preferred embodiment of the invention, the electrolysis of water and/or the separation of air is powered by renewable energy resulting in a further advantage of reduced $CO_2$ emission.

The invention claimed is:
1. Process for the co-production of methanol and ammonia in parallel, comprising the steps of:
  (a) providing a hydrocarbon feed stock;
  (b) preparing a separate hydrogen stream and a separate oxygen stream by electrolysis of water;

(c) preparing a separate oxygen stream and a separate nitrogen stream by separation of air;
(d) introducing at least part of the separate oxygen stream from step (b) and at least part of the separate oxygen from step (c) into an autothermal reformer;
(e) in the autothermal reformer, autothermal reforming the hydrocarbon feed stock from step (a) to a methanol synthesis gas comprising hydrogen and carbon oxides;
(f) converting the methanol synthesis gas to raw methanol in a methanol synthesis stage; and in parallel
(g) introducing the at least part of the separate hydrogen stream from step (b) and the separate nitrogen stream from step (c) into an ammonia synthesis loop, and converting the nitrogen and hydrogen stream to ammonia.

2. Process of claim 1, wherein module ($M=(H_2-CO_2)/(CO+CO_2)$) of the methanol synthesis gas from step (e) is adjusted to a value of between 1.9 and 2.2 by adding a part of the separate hydrogen stream from step (b) into the methanol synthesis gas from step (e).

3. Process of claim 1, wherein the separate hydrogen stream from step (b) and the separate nitrogen stream from step (c) are introduced into the ammonia synthesis loop in amounts to provide a molar ratio of the hydrogen to the nitrogen of 2.7-3.3.

4. Process of claim 1, wherein the electrolysis of water and/or the separation of air is powered by renewable energy.

\* \* \* \* \*